United States Patent [19]

West

[11] Patent Number: 5,123,839
[45] Date of Patent: Jun. 23, 1992

[54] AIR AND WATER HEATER FOR DENTAL INSTRUMENTS

[76] Inventor: Charles J. West, 667 Palm Ave., Suite A, Imperial Beach, Calif. 92032

[21] Appl. No.: 676,360

[22] Filed: Mar. 28, 1991

Related U.S. Application Data

[63] Continuation-in-part of Ser. No. 605,695, Oct. 29, 1990.

[51] Int. Cl.$^5$ .......................... A61C 3/00; A61C 19/00
[52] U.S. Cl. ........................................................ 433/32
[58] Field of Search ..................................... 433/27, 32

[56] References Cited

U.S. PATENT DOCUMENTS

| | | | |
|---|---|---|---|
| 636,090 | 10/1899 | Waterman et al. | 433/32 |
| 2,420,338 | 5/1947 | Page | 433/32 |
| 3,094,779 | 6/1963 | Boulsover et al. | 433/32 |
| 3,506,002 | 4/1970 | Maurer et al. | 433/32 |
| 4,184,064 | 1/1980 | Williams | 433/32 |
| 4,249,899 | 2/1981 | Davis | 433/32 |
| 4,699,589 | 5/1987 | Friedman et al. | 433/32 |
| 4,793,807 | 12/1988 | Friedman et al. | 433/80 |
| 4,944,675 | 7/1990 | Löhn | 433/32 |

Primary Examiner—John J. Wilson
Assistant Examiner—Cindy A. Cherichetti
Attorney, Agent, or Firm—David L. Baker

[57] ABSTRACT

A dental heating apparatus has a cylindrical housing and a heating element in a heating chamber. There is a first tube to transfer air from an air supply source and a second tube to transfer water from a water supply source to the dental tool. The first tube and the second tube enter a first end and exit a second end of the heating chamber. The first tube and the second tube are in a heat conducting contact with and coil around the heating element. There is a preheat temperature sensor in intimate contact with an inlet end of the first and second tube before the first and second tubes contact the heating element. The postheat temperature sensor is in intimate contact with an exit end of the first and second tubes after the first and second tubes break contact with the heating element. There is a heating element circuit connected to the heating element to supply power. A temperature sensor circuit is connected to the preheat and the postheat temperature sensor to provide power to the sensors and transmit electrical signals from the sensors to a temperature control module. The module regulates and displays the temperature of the air and water exiting the first and second tubes, respectively. There is a third tube to deliver drive air to and a fourth tube to exhaust the drive air from the dental tool. The housing may have a fiber optic cable passing through it. The separate tubings and wiring may be placed in a bundle of tubings for better thermal and electrical protection and for better handling.

10 Claims, 5 Drawing Sheets

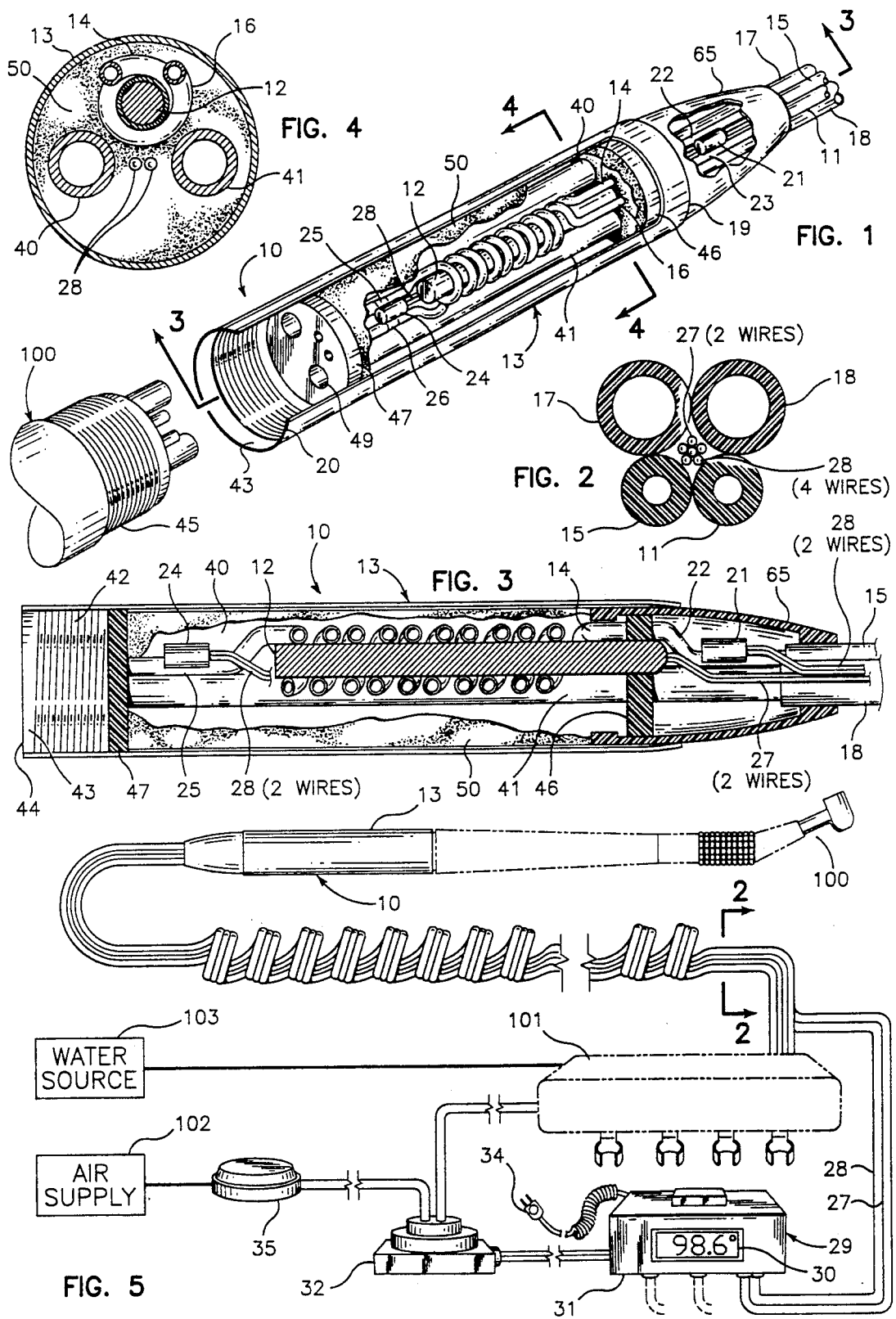

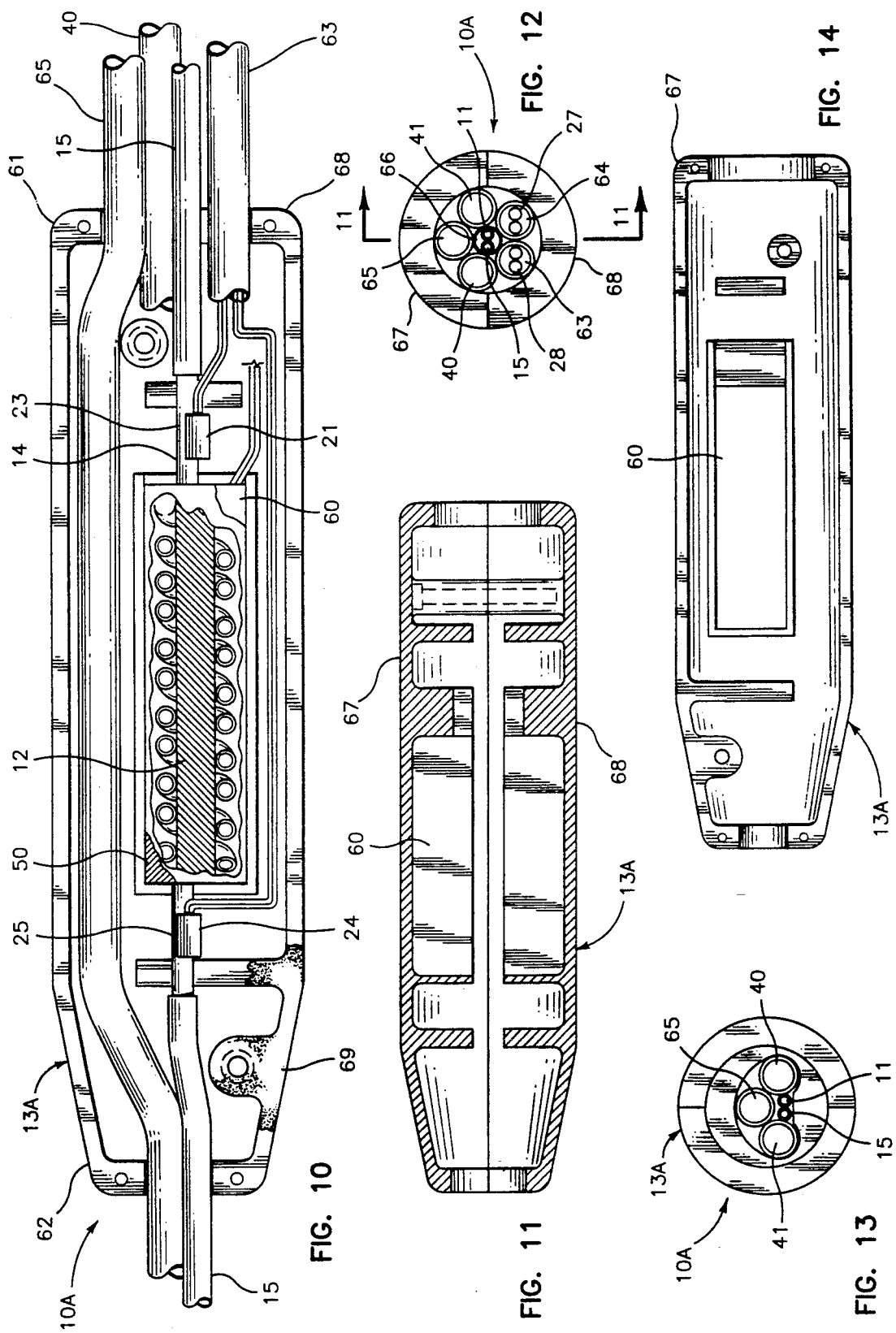

AIR AND WATER HEATER FOR DENTAL INSTRUMENTS

This invention is a continuation-in-part of application Ser. No. 07/605,695, filed on Oct. 28, 1990.

BACKGROUND OF THE INVENTION

1. Field of the Invention

The commercially available system now in use in the dental community provides a heated water reservoir which is located distant from the dental chair. The system requires several feet of tubing between the heated reservoir and the dental handpiece. One of the problems involved with this system is the long waiting time to flush out the cold water in the system before the heated water once again reaches the dental tool after the dental tool is stopped for even short periods of time. This waiting time increases the anxiety of the patient. The system is bulky and requires special plumbing and storage space for the heated reservoir. Many other systems have been tried but were found to be likewise inefficient and/or too expensive.

2. Description of the Related Art

U.S. Pat. No. 3,012,129 to G. E. Wehl on Dec. 5, 1961 shows a coolant heater and control unit which utilizes a sealed tank within a chamber and an electrical rod shaped heater coil to transmit heat to the water via metal fins. The temperature of the water is manually controlled by the user and the unit is too bulky to incorporate into a clinical setting.

U.S. Pat. No. 3,094,779 to G. Boulsover, et al., on Jun. 25, 1963 describes a dental handpiece having a heating chamber attached to the handpiece. The heating chamber is a reservoir type electric heater into which water and air are introduced, warmed and directed out of the chamber to be distributed. There is no temperature sensor provided. Lack of temperature control could lead to discomfort of the patient from the water.

U.S. Pat. No. 3,169,318 to W. C. Oaks on Feb. 16, 1965 shows an apparatus for supplying heated fluid to a dental handpiece. Static water in the handpiece is heated to the same temperature as the dynamic water. A water tank and heater with water flow adjustment valve is positioned distant the handpiece to control the water temperature to the handpiece. A separate tubing system keeps static heated water adjacent flowing water. The static water assists in keeping the dynamic water at a more constant temperature. The additional tubing is an inconvenience to an already crowded operatory area and the tubing allows the heat to dissipate rapidly from the water.

U.S. Pat. No. 4,184,064 to D. A. Williams on Jan. 15, 1980 shows a water heating means having a sealed air chamber through which a coiled tubing is passed. There is a wire filament heater element within the tubing. Water passes through the tubing and is heated by the element. The temperature sensor senses the temperature of the air outside of the coiled tube and thereby regulates the heat of the element and the water in the tubing.

U.S. Pat. No. 4,886,452 to G. Lohn on Dec. 12, 1989 describes a dental spray syringe handpiece that supplies heated air and water. The device has on/off, manually operated switches that operate separate heating chambers within an end of the syringe. The device cannot be incorporated to modify an existing syringe and is limited to a newly manufactured syringe designed to accommodate it.

SUMMARY OF THE INVENTION

One of the most important goals in the practice of dentistry is the reduction and elimination of pain and discomfort. From the beginning of dentistry, patients have associated pain and dentistry together. Most people avoid needed dental care because of their fear of expected pain. A major cause of pair is the flushing of cold water and air on sensitive areas of the teeth during drilling. A significant portion of this pain could be reduced if the water and air used to flush the tooth being repaired was maintained at near body temperature.

The heating apparatus transmits unheated compressed air to the dental handpiece turbine and transmits the exhaust air from the turbine to the atmosphere. The heating apparatus also transmits heated chip air and water to the dental tool. The pneumatic foot valve controls the flow of air and water. The dental tool has a mixing chamber to combine the chip air and water. The heating apparatus heats the chip air and water prior to the air and water being directed to the dental tool mixing chamber. The tubes that contain the chip water and air as they are heated by the heating element are usually composed of a suitable metal alloy that will transfer heat from the heating element to the air or water by conduction. The male tubular probes of the dental tool are designed to hermetically seat within the ports and tubes of the heating apparatus. The front and rear seals are usually chemically bonded to the cylindrical housing of the apparatus to reduce intrusion into the chamber containing the heating element. The insulation around the heater element may be injection molded or preformed and provides electrical and thermal insulation.

In the preferred embodiment, a heating apparatus in combination with a dental tool is described that has a cylindrical housing with a heating chamber inside. There is a heating element in the heating chamber. A first tube is in the cylindrical housing to transfer air from an air supply source to the dental tool. There is a second tube in the cylindrical housing to transfer water from a water supply source to the dental tool. The first tube and the second tube enter a first end of the heating chamber and exit a second end of the heating chamber through a port in each end of the cylindrical housing.

The first tube and the second tube are in a heat conducting contact with and coil around the heating element in the heating chamber. There is a preheat temperature sensor in intimate contact with an inlet end of the first tube and a inlet end of the second tube before the first and second tubes contact the heating element. A postheat temperature sensor is in intimate contact with an exit end of the first tube and an exit end of the second tube after the first and second tubes break contact with the heating element. The preheat and the post heat temperature sensors may be outside of the heating chamber but still inside the cylindrical housing. There is a heating element circuit connected to the heating element to supply current to the heating element. A temperature sensor circuit is connected to the preheat temperature sensor and to the postheat temperature sensor to provide current to the temperature sensors and to transmit electrical signals from the sensors to a temperature control module that regulates and displays the temperature of the air and water exiting the first and second tubes, respectively.

There is a third tube in the cylindrical housing to deliver drive air to the dental tool. The temperature control module has a housing. There is a pneumatically activated electrical switch connected to a temperature control module circuit in the housing. The temperature control module circuit selectively allows current flow from an AC power source. A pneumatic pressure switch is connected between a source of compressed air and the pneumatically activated electrical switch to pneumatically activate the electrical switch and to selectively allow air to flow from the air supply to the first tube and to the third tube. The pneumatic pressure also allows water to flow from the water supply source to the second tube. The pneumatically activated electrical switch allows current flow to the heating element only when the pneumatic pressure switch is activated.

An AC power amplifier, in the module circuit, regulates the amount of AC current received from the pneumatically activated electrical switch to the heating element circuit. There is an AC to DC convertor and circuit, in the module circuit, to receive AC power from the AC power supply and to provide DC current to the temperature control module circuit and the temperature sensor circuit. There is a temperature regulator and circuit, in the module circuit, to receive signals from the temperature sensors through the temperature sensor circuit and to regulate the duration of time the AC current is sent by the AC power amplifier to the heating element. A digital display means, in the module circuit, shows the temperature of the air and water exiting the first tube and second tube, respectively.

There is a fourth tube in the cylindrical housing to exhaust the drive air from the dental tool. A portion of the temperature sensor circuit is in a fifth tube and there is a portion of the heating element circuit in a sixth tube.

There may be a fiber optic cable enclosed in and passing through the cylindrical housing. There may be a portion of the first and second tubes enclosed in a seventh tube. There may be an insulation filling an air space in the heating chamber to reduce heat loss and provide electrical insulation. The cylindrical housing may have two longitudinal halves and there may a seal between the two halves to reduce heat loss from the heating chamber.

In a first alternative embodiment, a heating apparatus in combination with a dental tool is described that has a cylindrical housing and a heating element in the housing. There is no heating chamber set aside in the housing as in the preferred embodiment. There is a first tube in the cylindrical housing to transfer air from an air supply source to the dental tool and a second tube in the cylindrical housing to transfer water from a water supply source to the dental tool. The first tube and the second tube enter a first end of the cylindrical housing and exit a second end of the cylindrical housing. The first tube and the second tube are in a heat conducting contact with and coil around the heating element in the housing. There is a preheat temperature sensor in intimate contact with an inlet end of the first tube and an inlet end of the second tube before the first and second tubes contact the heating element. The postheat temperature sensor is in intimate contact with an exit end of the first tube and an exit end of the second tube after the first and second tubes break contact with the heating element. There is a heating element circuit connected to the heating element to supply power to the heating element. A temperature sensor circuit is connected to the preheat temperature sensor and to the postheat temperature sensor to provide current to the temperature sensors and to transmit electrical signals from the sensors to a temperature control module. The temperature control module regulates and displays the temperature of the air and water exiting the first and second tubes, respectively. There is a third tube in the cylindrical housing to deliver drive air to the dental tool and a fourth tube in the cylindrical housing to exhaust the drive air from the dental tool. A female thread is positioned in an inside wall near a front end of the cylindrical housing to mate with a male thread of the dental tool. There is a front seal and a rear seal in the cylindrical housing. There are a plurality of first ports in the rear seal to allow the tubes and a plurality of wires, in the temperature sensor circuit and in the heater element circuit, to pass through the rear seal. There are a plurality of second ports in the front seal to allow the tubes to pass through the front seal. An insulation fills the air space in the cylindrical housing between the front and the rear seal to reduce heat loss and to provide electrical insulation.

The temperature control module may have a housing. The module may have a pneumatically activated electrical switch connected to a temperature control module circuit, in the housing, to selectively allow current flow from an AC power source. A pneumatic pressure switch may be connected between a source of compressed air and the pneumatically activated electrical switch to pneumatically activate the electrical switch, and to selectively allow air to flow from the air supply to the first tube and to the third tube and to allow water to flow from the water supply source to the second tube. The pneumatically activated electrical switch may allow current flow to the heating element only when the pneumatic pressure switch is activated. The chip water and air is then heated very rapidly and there is almost no waiting time involved. There may be an AC power amplifier, in the module circuit, to regulate the amount of AC current received from the pneumatically activated electrical switch to the heating element circuit. There may be an AC to DC convertor and circuit, in the module circuit, to receive AC power from the AC power source and to provide DC current to the temperature control module circuit and the temperature sensor circuit. There may be a temperature regulator and circuit, in the module circuit, to receive signals from the temperature sensors through the temperature sensor circuit and to regulate an amount of AC current sent by the AC power amplifier to the heating element. There may be a digital display means, in the module circuit, to show the temperature of the air and water exiting the first tube and second tube, respectively.

In a second alternative embodiment, instead of placing the heating apparatus within a separate cylindrical housing attached to an existing dental tool, the apparatus could be placed within a dental tool housing at the time of manufacture of the dental tool.

It is an objective of this invention to provide a relatively inexpensive, easily installed and highly efficient in-line air/water heater apparatus for use with dental rotary instruments and air/water syringes.

It is another object of this invention to provide a heating apparatus that will reduce the apprehension of dental patients due to a reduction of pain, raise the patient comfort level and to reduce the need of anesthetic injections to counter the pain caused by cold water and air on exposed tooth dentin structure.

It is an objective of this invention to provide a heating apparatus with the ability to greatly reduce cycling of the heater controls which keeps the temperature range steady within the system.

It is another object to pro\`..;e a heating apparatus that may be used with existing air driven dental tools and that can be installed with little difficulty and be unobtrusive to the clinician.

It is another object of this invention to provide a heating apparatus wherein the air/water heating technology may be incorporated into the housing of an existing dental tool.

BRIEF DESCRIPTION OF THE DRAWINGS

FIG. 1 is a perspective view of the temperature controlled air and water heating apparatus for dental rotary instruments.

FIG. 2 is a cross-sectional view taken along lines 2—2 of FIG. 5.

FIG. 3 is a cross-sectional view taken along lines 3—3 of FIG. 1.

FIG. 4 is a cross-sectional view taken along lines 4—4 of FIG. 1.

FIG. 5 is a schematical view of the heating apparatus attached to the temperature monitor and the fluid and air flow control module means.

FIG. 10 is a partial view partly in section and partly in elevation of the preferred embodiment.

FIG. 11 is a partial cross-sectional view of the housing along lines 11—11 of FIG. 12.

FIG. 12 is a partial cross-sectional view of one end of the preferred embodiment.

FIG. 13 is a partial cross-sectional view of the other end of the preferred embodiment.

FIG. 14 is a plan view of one section of the housing of the preferred embodiment.

DESCRIPTION OF THE PREFERRED EMBODIMENT

Figure 6:
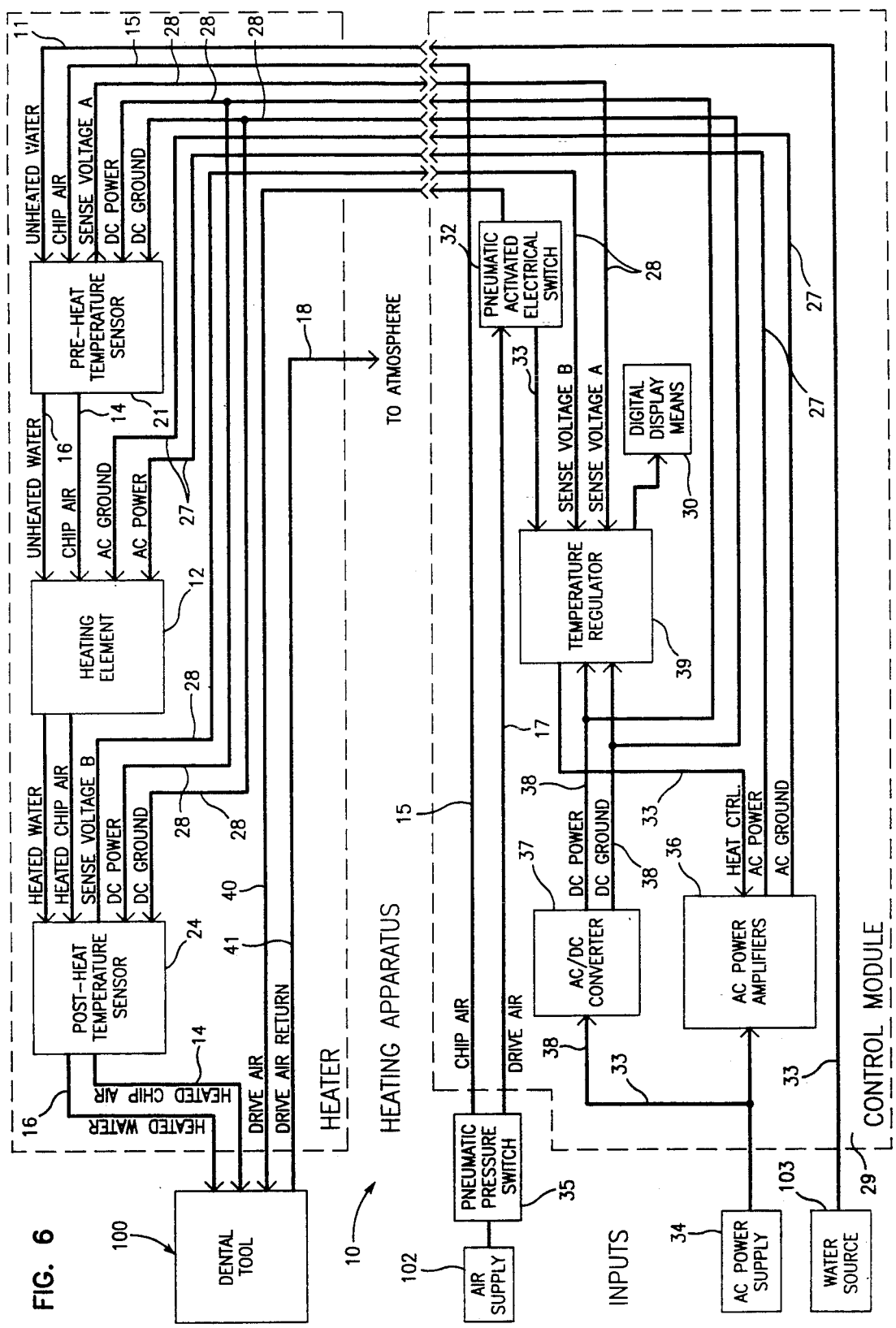
FIG. 6 is a flow and wiring schematic of the heating apparatus and the control module means.
Figure 7:
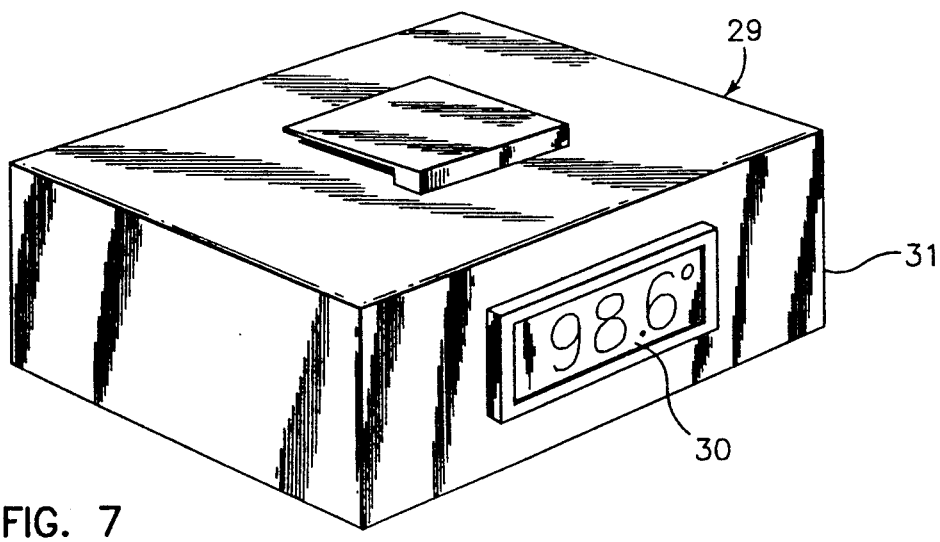
FIG. 7 is a top perspective view of the temperature module.
Figure 8:
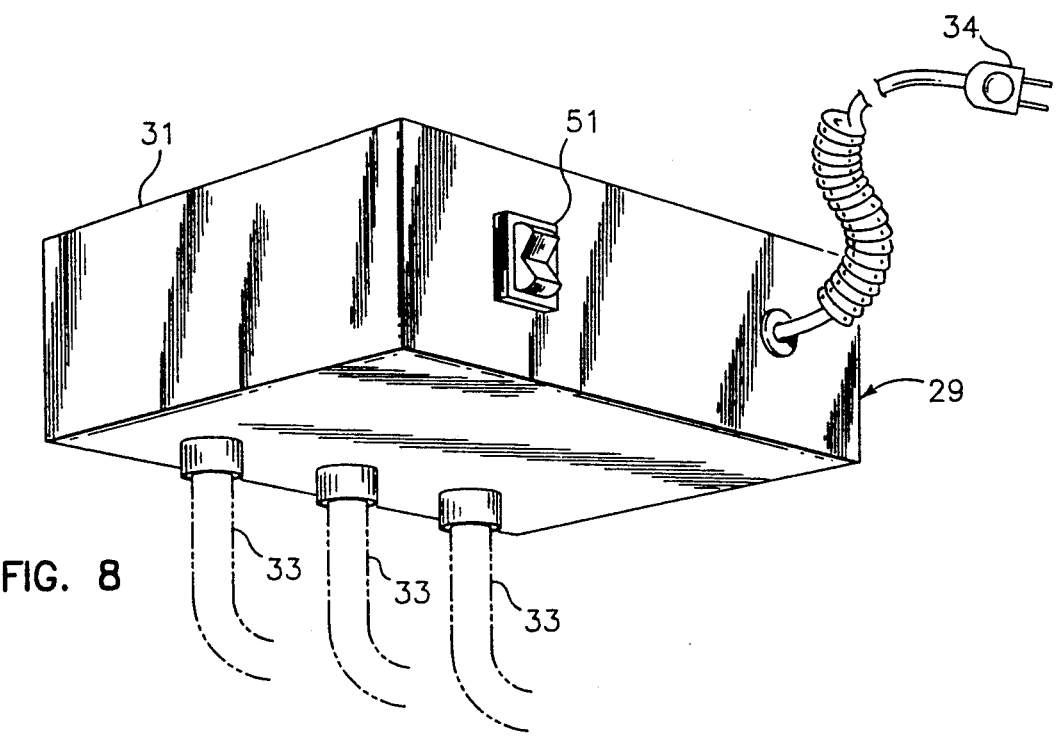
FIG. 8 is a bottom perspective view of the temperature module.
Figure 9:
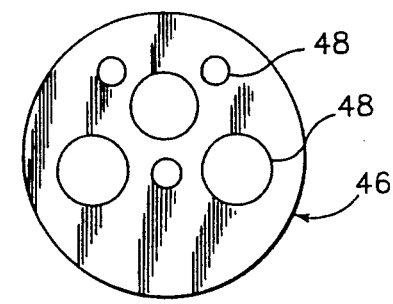
FIG. 9 is a plan view of the rear seal.
Figure 15:
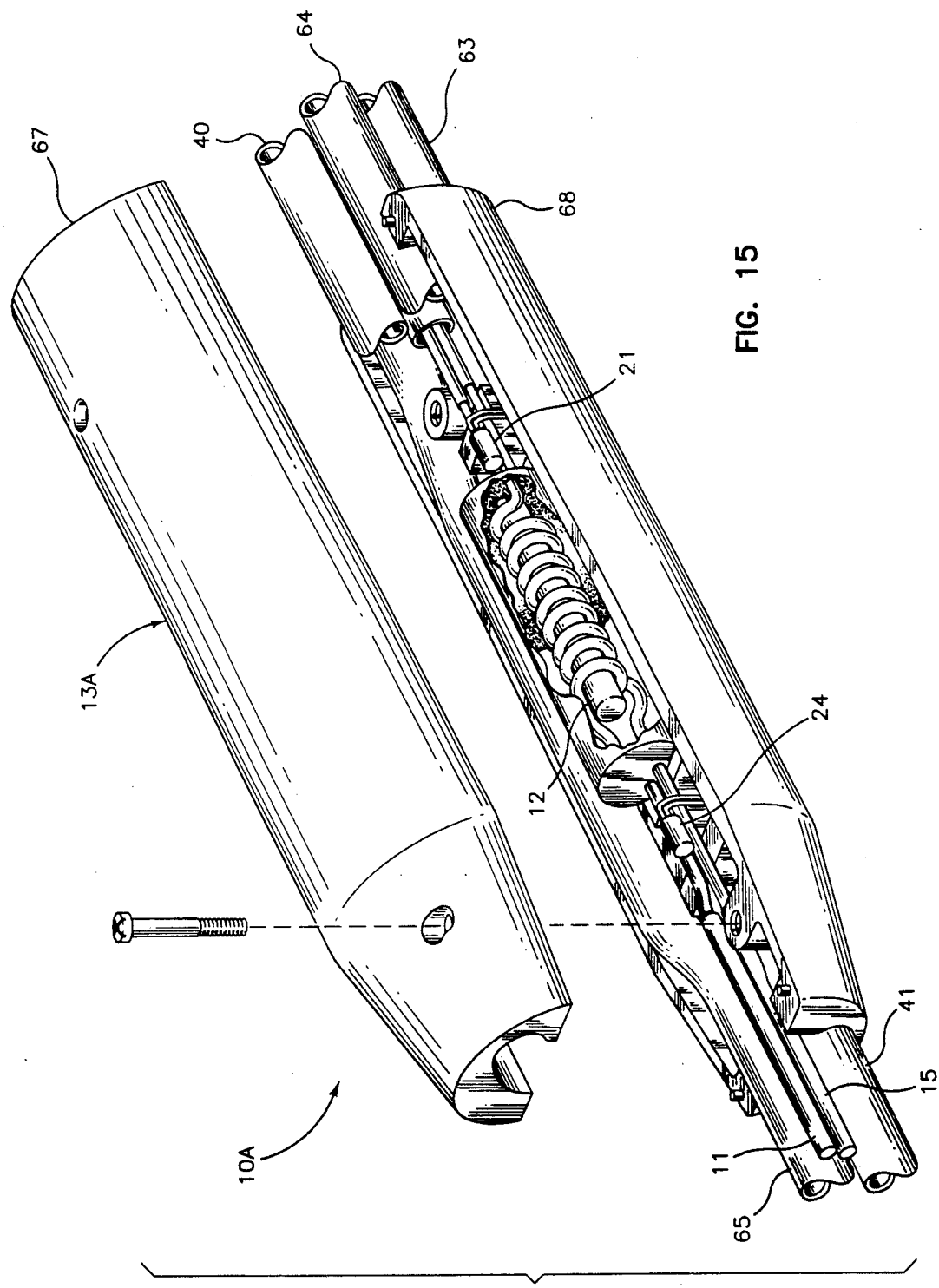
FIG. 15 is an exploded partial view of the preferred embodiment.

In FIGS. 1 through 15 is shown a heating apparatus 10 and 10a used in combination with a dental tool 100 or other dental tools such as a air/water syringe (not shown). Like elements of the preferred and alternative embodiments are identified by like numbers. Similar but differing elements are shown with an "A" along with the number.

In the preferred embodiment (See FIGS. 10 through 15), the heating apparatus 10A has a cylindrical housing 13A that has a heating chamber 60. There is a heating element 12 in the heating chamber 60. There is a first tube 14 to transfer chip air from an air supply source 102 to the dental tool 100, via a flexible eighth tube 15, and a second tube 16 to transfer water from a water source 103 via a flexible ninth tube 11 to the dental tool 100. Eighth tube 15 also transfers heated air from first tube 14 to the dental tool 100. Ninth tube 11 also transfers heated water from second tube 16 to the dental tube 100. The first tube 14 and the second tube 16 (made of metal) enter a first end 61 of the heating chamber 60 and exit a second end 62 of the heating chamber 60. The first tube 14 and the second tube 16 are in a heat conducting contact with and coil around the heating element 12 in the heating chamber 60.

There is a preheat temperature sensor 21 in intimate contact with an inlet end 22 of the first tube 14 and an inlet end 23 of the second tube 16 before the first and second tubes contact the heating element 12. The postheat temperature sensor 24 is in intimate contact with an exit end 25 of the first tube and a exit end of the second tube 16 after the first and second tubes break contact with the heating element 12. There is a heating element circuit 27 connected to the heating element 12 to supply current to the heating element. There is a temperature sensor circuit 28 connected to the preheat temperature sensor 21 and to the postheat temperature sensor 24 to provide current to the temperature sensors and transmit electrical signals from the sensors to a temperature control module 29.

The temperature control module 29 regulates and displays the temperature of the air and water, on LED display 30, exiting the first tube 14 and second tube 16, respectively. The temperature control module has a module housing 31. The module 29 has a pneumatically activated electrical switch 32 connected to a temperature control module circuit 33, in the housing 31, to selectively allow current flow from an AC power source 34.

There is a flexible third tube 40 in and passing through the cylindrical housing 13A, outside of the heating chamber 60, to deliver or transfer drive air to the dental tool 100 from the air supply 102. There is a pneumatical pressure switch 35 connected between a source of compressed air 102 and the pneumatically activated electrical switch 32 to pneumatically activate the electrical switch 32, and to selectively allow air to flow from the air supply 102 to the first tube 14 and to the third tube 40 and to allow water to flow from the water source 103 to the second tube 16. The pneumatically activated electrical switch 32 also activates and deactivates the heating element 12 so that electrical current is supplied to the heating element 12 only when the pneumatically activated switch 32 is activated. There is an AC power amplifier 36, in the module circuit 33, to regulate the amount of AC current received from the switch 32 to the heating element circuit 27. There is an AC to DC converter 37 and circuit 38, in the module circuit 33, to receive AC power from the AC power source 34 and to provide DC current to the temperature control module circuit 33 and the temperature sensor circuit 28. There is a temperature regulator and 39, in the module circuit 33, to receive signals from the temperature sensors 21 and 24 through the temperature sensor circuit 28 and to regulate the amount of the AC current that is sent by the AC power amplifier 36 to the heating element 12. There is a digital display means 30 in the module circuit 33 to show the averaged temperature of the air and water exiting the first tube 14 and second tube 16.

There is a flexible fourth tube 41 in and passing through the cylindrical housing 13A, outside of the heating chamber, to transfer the exhaust drive air from the dental tool 100. A portion of the temperature sensor circuit 28 is in a fifth tube 63. A portion of the heating element circuit 27 is in a sixth tube 64.

There is a fiber optic cable 65 that passes through the cylindrical housing 13A. There is a portion of the eighth tube 15 and ninth tube 11 in an seventh tube 66.

There is an insulation 50 filling an air space in the heating chamber 60 to reduce heat loss and provide electrical insulation. The cylindrical housing 13A has two longitudinal halves 67 and 68 and a seal 69 between the two halves to reduce heat loss from the heating chamber 60 and from the temperature sensors 21 and 24. There may be a vent hole (not shown) in housing 13A to vent excess heat.

In an alternative embodiment (See FIGS. 1 through 9), the heating apparatus 10 has a cylindrical housing 13 and a heating element 12 in the housing 13. There is a first tube 14 to transfer chip air from an air supply source 102 to the dental tool 100, via flexible tubing 15, and a second tube 16 to transfer water from a water source 103 via flexible tubing 11 to the dental tool 100. There is a third tube 40 in the heating apparatus 10 to transfer drive air to the dental tool 100 from the air supply 102 via flexible tubing 17. There is a fourth tube 41 in the heating apparatus 10 to transfer the exhaust drive air from the dental tool 100 and then to a flexible tubing 18. The first tube 14 and the second tube 16 enter a first end 19 of the cylindrical housing 13 and exit a second end 20 of the cylindrical housing 13. The first tube 14 and the second tube 16 are in a heat conducting contact with and coiling around the heating element 12 in the housing 13.

There is a preheat temperature sensor 21 in intimate contact with an inlet end 22 of the first tube 14 and an inlet end 23 of the second tube 16 before the first and second tubes contact the heating element 12. The postheat temperature sensor 24 is in intimate contact with an exit end 25 of the first tube and an exit end 26 of the second tube 16 after the first and second tubes break contact with the heating element 12. There is a heating element circuit 27 connected to the heating element 12 to supply current to the heating element. There is a temperature sensor circuit 28 connected to the preheat temperature sensor 21 and to the postheat temperature sensor 24 to provide current to the temperature sensors and transmit electrical signals from the sensors to a temperature control module 29. There is a protective boot 65 that could be made of an elastic material such as rubber or plastic. The boot 65 could also be made of a non-pliable material. The boot protects and provides access to the preheat temperature sensor and provides access to the points where the water and air flexible tubings connect to the tubes 14, 16, 40 and 41. The boot also helps to provide for access to and removal of the heating element, tubes, sensors and insulation.

The temperature control module 29 regulates and displays the temperature of the air and water, on LED display 30, exiting the first tube 14 and second tube 16, respectively. The temperature control module has a module housing 31. The module 29 has a pneumatically activated electrical switch 32 connected to a temperature control module circuit 33, in the housing 31, to selectively allow current flow from an AC power source 34.

There is a pneumatic pressure switch 35 connected between a source of compressed air 102 and the pneumatically activated electrical switch 32 to pneumatically activate the electrical switch 32, and to selectively allow air to flow from the air supply 102 to the first tube 14 and to the third tube 40 and to allow water to flow from the water source 103 to the second tube 16. The pneumatically activated electrical switch 32 also activates and deactivates the heating element 12 so that electrical current is supplied to the heating element 12 only when the pneumatically activated switch 32 is activated. There is an AC power amplifier 36, in the module circuit 33, to regulate the amount of AC current received from the pneumatically activated electrical switch 32 to the heating element circuit 27. There is an AC to DC convertor 37 and circuit 38, in the module circuit 33, to receive AC power from the AC power source 34 and to provide DC current to the temperature control module circuit 33 and the temperature sensor circuit 28. There is a temperature regulator 39, in the module circuit 33, to receive signals from the temperature sensors 21 and 24 through the temperature sensor circuit 28 and to regulate the amount of the AC current that is sent by the AC power amplifier 36 to the heating element 12. There is a digital display means 30 in the module circuit 33 to show the averaged temperature of the air and water exiting the first tube 14 and second tube 16.

There is a third tube 40 in the cylindrical housing 13 to deliver drive air to the dental tool 100 and a fourth tube 41 in the cylindrical housing 13 to exhaust the drive air from the dental tool 100. A female thread 42 is located in the inside wall 43 near a front end 44 of the cylindrical housing 13 to mate with a male thread 45 of the dental tool 100. There is a rear seal 46 in the cylindrical housing and a front seal 47 in the cylindrical housing 13. There are a plurality of first ports 48 in the rear seal 46 to allow the tubes and a plurality of wires in the temperature sensor circuit 28 and in the heater element circuit 27, to pass through the rear seal 46. There are a plurality of second ports 49 in the front seal 47 to allow the tubes (14, 16, 40 and 41) to pass through the front seal. An insulation 50 fills the air space in the cylindrical housing 13 between the rear seal 46 and the front seal 47 to reduce heat loss and provide electrical insulation. The module 31 has a manual on/off switch 51 in the module circuit to shut down the apparatus 10 when not in use. A fiber optic cable could be placed within the apparatus to connect with a fiber optic cable within the dental tool to provide light to the work surface.

The foregoing descriptions and drawings of the invention are explanatory and illustrative only, and various changes in shape, sizes and arrangements of parts as well certain details of the illustrated construction may be made within the scope of the appended claims without departing from the true spirit of the invention.

I claim:

1. A heating apparatus in combination with a dental tool comprising:
   a. a cylindrical housing;
   b. a heating element in the housing;
   c. a first tube in the cylindrical housing to transfer air from an air supply source to the dental tool;
   d. a second tube in the cylindrical housing to transfer water from a water supply source to the dental tool;
   e. the first tube and the second tube entering a first end of the cylindrical housing and exiting a second end of the cylindrical housing;
   f. the first tube and the second tube in a heat conducting contact with and coiling around the heating element in the housing;
   g. a preheat temperature sensor in intimate contact with an inlet end of the first tube and an inlet end of the second tube before the first and second tubes contact the heating element;

h. a postheat temperature sensor in intimate contact with an exit end of the first tube and an exit end of the second tube after the first and second tubes break contact with the heating element;
i. a heating element circuit connected to the heating element to supply current to the heating element;
j. a temperature sensor circuit connected to the preheat temperature sensor and to the postheat temperature sensor to provide current to the temperature sensors and transmit electrical signals from the sensors to a temperature control module that regulates and displays the temperature of the air and water exiting the first and second tubes, respectively;
k. a third tube in the cylindrical housing to deliver drive air to the dental tool;
the temperature control module further comprises:
a housing;
a pneumatically activated electrical switch connected to a temperature control module circuit, in the housing, to selectively allow current flow from an AC power source;
a pneumatic pressure switch connected between a source of compressed air and the pneumatically activated electrical switch to pneumatically activate the electrical switch, and to selectively allow air to flow from the air supply to the first tube and to the third tube and to allow water to flow from the water supply source to the second tube;
an AC power amplifier, in the module circuit, to regulate the amount of AC current received from the switch to the heating element circuit;
an AC to DC convertor and circuit, in the module circuit, to receive AC power from the AC power supply and to provide DC current to the temperature control module circuit and the temperature sensor circuit;
a temperature regulator and circuit, in the module circuit, to receive signals from the temperature sensors through the temperature sensor circuit and regulate the duration of time the AC current is sent by the AC power amplifier to the heating element; and
a digital display means, in the module circuit, to show the temperature of the air and water exiting the first tube and second tube, respectively;
l. a fourth tube in the cylindrical housing to exhaust the drive air from the dental tool;
m. a female thread in an inside wall near a front end of the cylindrical housing to mate with a male thread of the dental tool;
n. a front seal in the cylindrical housing;
o. a rear seal in the cylindrical housing;
p. a plurality of first ports in the rear seal to allow the tubes and a plurality of wires in the temperature sensor circuit and in the heater element circuit to pass through the rear seal;
q. a plurality of second ports in the front seal to allow the tubes to pass through the front seal; and
r. an insulation filling an air space in the cylindrical housing between the front and the rear seal to reduce heat loss and provide electrical insulation.

2. A heating apparatus as described in claim 1 wherein the temperature control module further comprises the pneumatically activated electrical switch allowing current flow to the heating element only when the pneumatic pressure switch is activated.

3. A heating apparatus in combination with a dental tool comprising:
a. a cylindrical housing;
b. a heating element in the housing;
c. a first tube in the cylindrical housing to transfer air from an air supply source to the dental tool;
d. a second tube in the cylindrical housing to transfer water from a water supply source to the dental tool;
e. the first tube and the second tube entering a first end of the cylindrical housing and exiting a second end of the cylindrical housing;
f. the first tube and the second tube in a heat conducting contact with and coiling around the heating element in the housing;
g. a preheat temperature sensor in intimate contact with an inlet end of the first tube and an inlet end of the second tube before the first and second tubes contact the heating element;
h. a postheat temperature sensor in intimate contact with an exit end of the first tube and an exit end of the second tube after the first and second tubes break contact with the heating element;
i. a heating element circuit connected to the heating element to supply current to the heating element;
j. a temperature sensor circuit connected to the preheat temperature sensor and to the postheat temperature sensor to provide current to the temperature sensors and transmit electrical signals from the sensors to a temperature control module that regulates and displays the temperature of the air and water exiting the first and second tubes, respectively;
k. a third tube in the cylindrical housing to deliver drive air to the dental tool;
the temperature control module further comprises:
a housing;
a pneumatically activated electrical switch connected to a temperature control module circuit, in the housing, to selectively allow current flow from an AC power source;
a pneumatic pressure switch connected between a source of compressed air and the pneumatically activated electrical switch to pneumatically activate the electrical switch, and to selectively allow air to flow from the air supply to the first tube and to the third tube and to allow water to flow from the water supply source to the second tube;
the pneumatically activated electrical switch allowing current flow to the heating element only when the pneumatic pressure switch is activated.
an AC power amplifier, in the module circuit, to regulate the amount of AC current received from the switch to the heating element circuit;
an AC to DC convertor and circuit, in the module circuit, to receive AC power from the AC power supply and to provide DC current to the temperature control module circuit and the temperature sensor circuit;
a temperature regulator and circuit, in the module circuit, to receive signals from the temperature sensors through the temperature sensor circuit and regulate the duration of time the AC current is sent by the AC power amplifier to the heating element; and a digital display means, in the module circuit, to show the temperature of the air and water exiting the first tube and second tube, respectively;

l. a fourth tube in the cylindrical housing to exhaust the drive air from the dental tool;

m. a female thread in an inside wall near a front end of the cylindrical housing to mate with a male thread of the dental tool;

n. a front seal in the cylindrical housing;

o. a rear seal in the cylindrical housing;

p. a plurality of first ports in the rear seal to allow the tubes and a plurality of wires in the temperature sensor circuit and in the heater element circuit to pass through the rear seal;

q. a plurality of second ports in the front seal to allow the tubes to pass through the front seal; and r. an insulation filling an air space in the cylindrical housing between the front and the rear seal to reduce heat loss and provide electrical insulation.

4. A heating apparatus in combination with a dental tool comprising:

a. a cylindrical housing having a heating chamber;

b. a heating element in the heating chamber;

c. a first tube in the cylindrical housing to transfer air from an air supply source to the dental tool;

d. a second tube in the cylindrical housing to transfer water from a water supply source to the dental too;

e. the first tube and the second tube entering a first end of the heating chamber and exiting a second end of the heating chamber;

f. the first tube and the second tube in a heat conducting contact with and coiling around the heating element in the heating chamber;

g. a preheat temperature sensor in intimate contact with an inlet end of the first tube and an inlet end of the second tube before the first and second tubes contact the heating element;

h. a postheat temperature sensor in intimate contact with an exit end of the first tube and an exit end of the second tube after the first and second tubes break contact with the heating element;

i. a heating element circuit connected to the heating element to supply current to the heating element;

j. a temperature sensor circuit connected to the preheat temperature sensor and to the postheat temperature sensor to provide current to the temperature sensors and transmit electrical signals from the sensors to a temperature of the air and water exiting the first and second tubes, respectively;

k. a third tube in the cylindrical housing to deliver drive air to the dental tool;

the temperature control module further comprises:
a housing;
a pneumatically activated electrical switch connected to a temperature control module circuit, in the housing, to selectively allow current flow from an AC power source;
a pneumatic pressure switch connected between a source of compressed air and the pneumatically activated electrical switch to pneumatically activate the electrical switch, and to selectively allow air to flow from the air supply to the first tube and to the third tube and to allow water to flow from the water supply source to the second tube;

an AC power amplifier, in the module circuit, to regulate the amount of AC current received from the pneumatically activated electrical switch to the heating element circuit;
an AC to DC convertor and circuit, in the module circuit, to receive AC power from the AC power supply and to provide DC current to the temperature control module circuit and the temperature sensor circuit;
a temperature regulator and circuit, in the module circuit, to receive signals from the temperature sensors through the temperature sensor circuit and regulate the duration of time the AC current is sent by the AC power amplifier to the heating element;
a digital display means, in the module circuit, to show the temperature of the air and water exiting the first tube and second tube, respectively; and l. a fourth tube in the cylindrical housing to exhaust the drive air from the dental tool;

m. a portion of the temperature sensor circuit in a fifth tube; and n. a portion of the heating element circuit in a sixth tube.

5. A heating apparatus as described in claim 4 wherein the temperature control module further comprises the pneumatically activated electrical switch allowing current flow to the heating element only when the pneumatic pressure switch is activated.

6. A heating apparatus in combination with a dental tool comprising:

a. a cylindrical housing having a heating chamber;

b. a heating element in the heating chamber;

c. a first tube in the cylindrical housing to transfer air from an air supply source to the dental tool;

d. a second tube in the cylindrical housing to transfer water from a water supply source to the dental tool;

e. the first tube and the second tube entering a first end of the heating chamber and exiting a second end of the heating chamber;

f. the first tube and the second tube in a heat conducting contact with and coiling around the heating element in the heating chamber;

g. a preheat temperature sensor in intimate contact with an inlet end of the first tube and an inlet end of the second tube before the first and second tubes contact the heating element;

h. a postheat temperature sensor in intimate contact with an exit end of the first tube and an exit end of the second tube after the first and second tubes break contact with the heating element;

i. a heating element circuit connected to the heating element to supply current to the heating element;

j. a temperature sensor circuit connected to the preheat temperature sensor and to the postheat temperature sensor to provide current to the temperature sensors and transmit electrical signals from the sensors to a temperature control module that regulates and displays the temperature of the air and water exiting the first and second tubes, respectively;

k. a third tube in the cylindrical housing, to deliver drive air to the dental tool;
the temperature control module further comprises:
a housing;

a pneumatically activated electrical switch connected to a temperature control module circuit, in the housing, to selectively allow current flow from an AC power source;

a pneumatic pressure switch connected between a source of compressed air and the pneumatically activated electrical switch to pneumatically activate the electrical switch, and to selectively allow air to flow from the air supply to the first tube and to the third tube and to allow water to flow from the water supply source to the second tube;

the pneumatically activated electrical switch allowing current flow to the heating element only when the pneumatic pressure switch is activated;

an AC power amplifier, in the module circuit, to regulate the amount of AC current received from the pneumatically activated electrical switch to the heating element circuit;

an AC to DC convertor and circuit, in the module circuit, to receive AC power from the AC power supply and to provide DC current to the temperature control module circuit and the temperature sensor circuit;

a temperature regulator and circuit, in the module circuit, to receive signals from the temperature sensors through the temperature sensor circuit and regulate the duration of time the AC current is sent by the AC power amplifier to the heating element;

a digital display means, in the module circuit, to show the temperature of the air and water exiting the first tube and second tube, respectively; and l. a fourth tube in the cylindrical housing to exhaust the drive air from the dental tool;

m. a portion of the temperature sensor circuit in a fifth tube; and n. a portion of the heating element circuit in a sixth tube.

7. A heating apparatus as described in claim 6 further comprising a fiber optic cable passing through the cylindrical housing.

8. A heating apparatus as described in claim 6 further comprising a portion of the first and second tubes in a seventh tube.

9. A heating apparatus as described in claim 6 wherein the heating chamber further comprises an insulation filling an air space in the heating chamber to reduce heat loss and provide electrical insulation.

10. A heating apparatus as described in claim 6 wherein the cylindrical housing comprises:

a. two longitudinal halves; and b. a seal between the two halves to reduce heat loss from the heating chamber.

* * * * *